(12) United States Patent
Tao et al.

(10) Patent No.: US 6,610,953 B1
(45) Date of Patent: Aug. 26, 2003

(54) ITEM DEFECT DETECTION APPARATUS AND METHOD

(75) Inventors: Yang Tao, Fayetteville, AR (US); Zhiqing Wen, Fayetteville, AR (US)

(73) Assignee: University of Arkansas, Little Rock, AR (US)

( * ) Notice: Subject to any disclaimer, the term of this patent is extended or adjusted under 35 U.S.C. 154(b) by 0 days.

(21) Appl. No.: 09/350,640

(22) Filed: Jul. 9, 1999

Related U.S. Application Data

(63) Continuation-in-part of application No. 09/046,454, filed on Mar. 23, 1998, now abandoned, which is a continuation-in-part of application No. 09/046,270, filed on Mar. 23, 1998, now Pat. No. 6,271,520.
(60) Provisional application No. 60/092,312, filed on Jul. 9, 1998.

(51) Int. Cl.$^7$ ................................................ B07C 5/00
(52) U.S. Cl. ........................ 209/577; 209/11; 209/580; 209/587; 250/330; 250/341.6
(58) Field of Search ............................. 209/3, 11, 576, 209/577, 580, 581, 587, 938, 939; 382/110, 156; 250/330, 341.6

(56) References Cited

U.S. PATENT DOCUMENTS

| | | | |
|---|---|---|---|
| 2,994,428 A | 8/1961 | Daubendick | 209/111.5 |
| 3,563,378 A | 2/1971 | Myers | 209/111.7 |

(List continued on next page.)

OTHER PUBLICATIONS

Zhiqing Wen and Yang Tao, Dual–wavelength imaging for on–line identification of stem–ends and calyxes, Dept. of Biological & Agricultural Engineering, University of Arkansas, Fayetteville, Arkansas, 1998.

Y. Tao, Z. Wen, An Adaptive Spherical Image Transform for High–Speed Fruit Defect Detection, 1999 American Society of Agricultural Engineers, vol. 42(1):241–246.

(List continued on next page.)

*Primary Examiner*—Tuan N. Nguyen
(74) *Attorney, Agent, or Firm*—Head, Johnson and Kachigian

(57) ABSTRACT

A method and apparatus is provided which addresses the drawbacks of the prior art and which incorporates two separate imaging devices, one near-infrared and one mid-infrared imaging device which simultaneously capture images of the passing objects. The background information is removed and images of the objects remain. A spherical optical transform and a defect preservation transform preserve any defect levels on objects and compensate for the non-lambertian gradient reflectants on spherical objects at their curvatures and dimensions. The processed images provided by the mid-infrared camera are subtracted from the images provided by the near-infrared camera to produce an image of just defects which are analyzed to produce the separation or sorting control signals based on defect rejection decisions and user parameters to signal appropriate mechanical actions (driver commands) to separate objects with defects from those that do not contain defects, or to sort or categorize objects based on the amount, type, size, or character of the defects. At least a portion of the exterior surface of each item or object to be inspected must be raised by about 5–15° C. or more so that the cameras can provide an image of a difference in temperature between outer smooth healthy surface and the cavity at the stem-end, the stem, and calyx of an apple or a similar depression, cavity, protrusion, or the like in another object or item. In accordance with one embodiment of the present invention, heated brush rollers are used to quickly heat the exterior of apples passing along a conveyor to provide the necessary change in temperature to allow the cameras to provide an image of defects, stem-end, stem, and/or calyx.

3 Claims, 22 Drawing Sheets

U.S. PATENT DOCUMENTS

| | | | | |
|---|---|---|---|---|
| 3,859,522 A | | 1/1975 | Cuthbert | 250/233 |
| 4,244,475 A | | 1/1981 | Green | 209/588 |
| 4,417,663 A | | 11/1983 | Suzuki | 209/587 |
| 4,532,723 A | | 8/1985 | Kellie et al. | 356/73 |
| 5,013,906 A | | 5/1991 | Miyakawa et al. | 250/223 |
| 5,197,585 A | | 3/1993 | Blood | 198/384 |
| 5,339,963 A | | 8/1994 | Tao | 209/581 |
| 5,397,004 A | | 3/1995 | Kaiser et al. | 209/577 |
| 5,533,628 A | | 7/1996 | Tao | 209/580 |
| 5,621,215 A | | 4/1997 | Waldroup et al. | 250/461.2 |
| 5,659,624 A | * | 8/1997 | Fazzari et al. | 382/110 |
| 5,732,147 A | | 3/1998 | Tao | 382/110 |
| 5,884,775 A | * | 3/1999 | Campbell | 209/581 |

OTHER PUBLICATIONS

Zhiqing Wen, Yang Tao, Building a rule–based machine–vision system for defect inspection on apple sorting and packing lines, Expert Systems with Applications 16 (1999) 307–313.

Yang Tao, Spherical transform of fruit images for on–line defect extraction of mass objects, Optical Engineering, vol. 35, No. 2, Feb. 1996, pp. 344–350.

* cited by examiner (a)

(b)

(c)

ITEM DEFECT DETECTION APPARATUS AND METHOD

CROSS-REFERENCE TO RELATED APPLICATIONS

Priority is claimed to and this application is a continuation-in-part of U.S. provisional patent application Serial No. 60/092,312, filed Jul. 9, 1998, and is also a continuation-in-part of U.S. patent application Ser. No. 09/046,454, filed Mar. 23, 1998, abandoned, and U.S. patent application Ser. No. 09/046,270, filed Mar. 23, 1998, U.S. Pat. No. 6,271,520.

STATEMENT REGARDING FEDERALLY SPONSORED RESEARCH OR DEVELOPMENT

This application may be subject to license rights of the U.S. Government and in particular the U.S. Department of Agriculture (USDA).

BACKGROUND OF THE INVENTION

The present invention is directed to a defect inspection system and, more particularly, high speed defect detection utilizing near and mid-infrared imaging, high speed image processing, comparison and contrast, processed image evaluation and characterization, and the development of control signals for sorting or separating objects or items based on the defect determination. More particularly, the present invention relates to methods of near and mid-infrared imaging for fruit defect inspection and fruit stem-end and calyx identification.

U.S. Pat. Nos. 5,339,963 and 5,533,628 each issued to Yang Tao and assigned to Agri-Tech, Inc., are each hereby incorporated by reference, and describe methods and apparatus for sorting objects by color, and in particular are directed to the sorting of apples. The color sorting apparatus has a singulator section, a color sorter, and a conveyor which drops the sorted objects into appropriate collection bins. The objects for sorting are transported on an endless conveyor through the singulation and color sorting section. An independently adjustable speed belt rotates in the same direction as the wheels and operates to provide a view of each of the four sides of the object to an imaging device such as a camera which supplies red, green and blue signals to an image processor which performs a color transformation and obtains a single composite hue value for each object or piece of fruit to be sorted. Based on a comparison of the hue value to the user program grading criteria, signals are provided to the conveyor so that the objects are ultimately deposited in the appropriate sorting bins.

U.S. Pat. No. 5,732,147, issued to Yang Tao and assigned to Agri-Tech, Inc., is hereby incorporated by reference and describes an image processing system using cameras and image processing techniques to identify undesirable objects on roller conveyor lines. The cameras above the conveyor capture images of the passing objects (such as apples). The roller background information is removed and images of the objects remain. To analyze each individual object accurately, the adjacent objects are isolated and small noisy residue fragments are removed. A spherical optical transformation and a defect preservation transformation preserve any defect levels on objects even below the roller background and compensate for the non-lambertian gradient reflectants on spherical objects at their curvatures and dimensions. Defect segments are then extracted from the resulting transformed images. The size, level and pattern of the defect segments indicate the degree of defects in the object. The extracted features are fed into a recognition process in a decision-making system for grade rejection decisions. The locations and coordinates of the defects generated by defect allocation function are combined with defect rejection decisions and user parameters to signal appropriate mechanical actions such as to separate objects with defects from those that do not contain defects.

Conventional attempts at using laser scanning and reflectance to detect line shifts or changes in height of the object in order to attempt to detect defects in fruit or other objects have not been successful and are not accurate due to the inability to provide the same orientation of each object, changes in size and shape between individual pieces or items of fruit, and the like.

Still further, it has been difficult to differentiate between true defects such as bruises, limb rub, bulls-eyes, fungus such as black net, blemishes, cuts, injuries, stem punches, cracks, worm holes, insect damage, disease damage, color defects, Russet and the like from the fruit stem-end, stem, calyx, or blossom. Hence, there is a need for an improved method and apparatus for defect detection, fruit, such as apple, defect detection as compared to detection of the stem-end, stem, and/or calyx identification, defects in smooth surfaces, and/or defect detection and object or item sorting or separation based thereon.

BRIEF SUMMARY OF THE INVENTION

In accordance with the present invention, a method and apparatus is provided which addresses the drawbacks of the prior art and which incorporates two separate imaging devices, one near-infrared and one mid-infrared imaging device which simultaneously capture images of the passing objects or items. The background information is removed and images of the objects remain. A spherical optical transform and a defect preservation transform preserve any defect levels on objects and compensate for the non-lambertian gradient reflectants on spherical objects at their curvatures and dimensions.

The mid-infrared or middle infrared camera is used at about 3–5 microns or 8–12 microns to provide an image of the stem-end, stems, and/or calyx but is insensitive to true defects. Near-infrared at about 700–1000 nanometers (nn) is used to provide an image of stem-end, stems, calyx, and defects.

In accordance with the present invention, the processed images provided by the mid-infrared camera are subtracted from the images provided by the near-infrared camera to produce an image of just defects which are analyzed to produce the item or object separation or sorting control signals based on defect rejection decisions and user parameters to signal appropriate mechanical actions (driver commands) to separate objects with defects from those that do not contain defects, or to sort or categorize objects based on the amount, type, size, or character of the defects.

In accordance with the present invention, a complete defect detection system for sorting, separating, or grading apples can be constructed for about $100,000.00 or less. In as much as the present invention is based on the use of infrared imaging devices, such as cameras, the temperature of at least a portion of the exterior surface of each item or object to be inspected must be raised by about 5–15° C. or more so that the cameras can provide an image of a difference in temperature between outer smooth surface and the cavity at the stem-end, the stem, and calyx of an apple or a similar depression, cavity, protrusion, or the like in another object or item. In accordance with one embodiment of the present invention, heated brush rollers are used to quickly heat the exterior of apples passing along a conveyor to provide the necessary change in temperature to allow the cameras to provide an image of defects, stem-end, stem, and/or calyx.

Although the present invention is especially adapted for use in inspecting and detecting defects in items or objects, such as apples and other fruits and vegetables such as pears, tomatoes, peaches, apricots, and other stone or pit foods having stem ends, stems, blossom ends, calyx, or the like, the present invention also finds applicability in inspecting and detecting defects in other items or objects, such as manufactured parts such as cups, dishes, balls, golf balls, bearings, molded plastic items, and the like having smooth surfaces, pits, posts, or the like.

The present invention provides a system which is effective, fast, has high resolution, and which has a greater accuracy and discrimination rate than prior art devices or systems.

The principal object of the present invention is the provision of a method and apparatus for the detection and discrimination of defects in items or objects such as apples.

Another object of the present invention is the provision of a method and apparatus for sorting items or objects based on the character, number, type or aggregation of defects.

A still further object of the present invention is the provision of a method and apparatus for discriminating between stem-end, stems, and calyx as compared to true defects.

Other objects and further scope of the applicability of the present invention will become apparent from the detailed description to follow, taken in conjunction with accompanying drawings wherein like parts are designated by like reference numerals.

DETAILED DESCRIPTION OF THE INVENTION

Figure 1A:
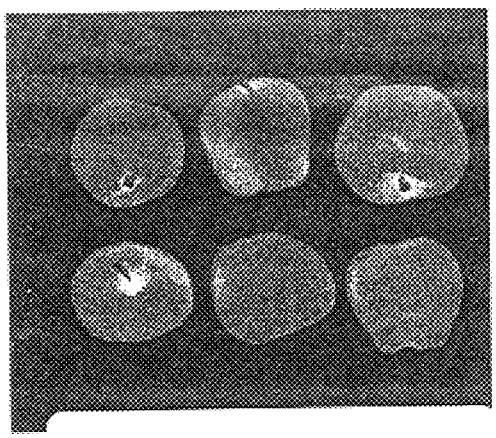
FIGS. 1–8, 15, 23, 24, 25, and 28 are photographic representations or illustrations.

In accordance with the present invention there is provided a method and apparatus utilizing simultaneous mid and near-infrared imaging to detect true defects on items or objects such as fruits and vegetables. The present invention solves the difficult problem that scientists and engineers have been having for more than twenty years of not being able to separate the images of stem-end, stem, and calyx from defects in fruit. In accordance with the present invention, one is able to easily discriminate between true defects and the stem-end, stem and calyx and is also able to accurately inspect both large and small defects.

Since stem-end, stem and calyx appear similar to true defects in images produced by imaging devices such as infrared cameras, they have in the past created tremendous confusion. The near-infrared (NIR) range from about 750 nanometers to 1200 nanometers (nm) is sensitive to defects on fruit. However, near-infrared cameras also pick up stem-end, stem and calyx. Separation of true defects from stem-end, stem, and/or calyx using only near-infrared is very difficult.

In accordance with the present invention, by using mid-infrared or middle infrared (MIR) in the 3 to 12 um range (micrometer or micron range with the exception of the 5 to 8 um range which is sensitive to hot air) which is insensitive to defects but sensitive to stems, stem-end and calyx, one is able to subtract the mid-infrared camera image from the near-infrared image (NIR-MIR) and obtain an image of only true defects.

Further, since most fruit is stored in controlled atmosphere storage (CA) where the temperature is controlled at about 4° C. typically for fruit like apples, heated brushes such as roller brushes or other types of brushes or rollers which can be heated by hot air, steam, liquid, or other sources such as hot fluid, hot air, heat lamps, or the like, are used to heat the fruit surface sufficiently to provide a change in temperature between the exterior smooth outer surface of the fruit and the stem-end cavity, the calyx, rot, bruise, limb rub, bulls-eyes, fungi such as black net, blemishes, cuts, injuries, stem punches, cracks, worm holes, insect damage, disease damage, color defects such as Russet, and the like which allow the mid-infrared camera to detect stem-end, stems, and calyx and allow the near-infrared camera to detect stem-end, stem, calyx, and true defects. Although heated brushes are preferred to speed up the process of increasing the temperature of the outer smooth surface of the fruit or other item or object being inspected, exposure to room temperature also enhances the change in temperature or delta-T between the cavities, pits, cracks, stem-end, calyx, stem, and the like with respect to the temperature of the smooth healthy outer surface of the fruit.

The present invention is useful in item or object defect detection and/or determination, especially fruit defect detection, defected fruit sorting, separating, and/or grading, stem-end or calyx identification, cavity spot identification, object detect or deformation identification, and the like.

The present invention is also easily retrofitted to existing or conventional fruit processing and/or packing systems or apparatus. As described in U.S. Pat. Nos. 5,339,963, 5,533, 628, and 5,732,147, herein incorporated by reference, although some aspects of the fruit packing process are already automated, much of it is still left to manual laborers. The automated equipment that is currently available is generally limited to conveyor systems and systems for measuring the color, size, and weight of apples.

A system manufactured by Agri-Tech, Inc. of Woodstock, Va. automates certain aspects of the apple packing process. At a first point in the packing system, apples are floated in large cleaning tanks. The apples are then elevated out of the tank by conveyors onto an inspection table. Workers alongside the table inspect the apples and eliminate any unwanted defective apples and other foreign material such as leaves, stems, and the like. The remaining apples are then fed on conveyors to cleaning, waxing and drying equipment. After being dried, the apples are sorted according to color, size, and shape and then packaged according to the sort.

As described in U.S. Pat. No. 5,732,147, the inspection process, a key step in the apple packing process, is still conventionally done by hand. Along the apple conveyors in the early cleaning process, workers are positioned to visually inspect the passing apples and remove the apples with defects such as apples with rot, apples that are injured, diseased, or seriously bruised, and other defective apples as well as foreign materials. These undesirable objects especially rotted and diseased apples, must be removed in the early stage (before coating) to prevent contamination of good fruit and reduce cost and successive processing. This manual apple inspection process is labor intensive, difficult, fatiguing, and subject to human error which allows misinspected apples to pass through the line.

Further, apples are graded in part according to the amount and extent of defects. In Washington state, for example, apples with defects are used for processing and to make into applesauce or juice. These apples usually cost less than apples with no defects or only a few defects. Apples that are not used for processing, known as fresh market apples, are also graded on the size of any defects and also on the number of defects.

In accordance with the present invention, an item or object defect identification, inspection, sorting, grading, and separation system is provided which automates the conventional manual inspection process. Further, the present infrared camera system can replace conventional laser inspection and defect detection systems which are more costly, subject to error, and difficult to implement with certain items such as fruit and the like which have irregular contours, shapes, features, and the like. The present method and apparatus does not require that each item or object be oriented similarly to provide for defect detection, inspection, and object grading, sorting, or separation.

Still further, the present invention incorporates patented or state of the art image transformation or processing which transforms a curved or spherical image to a flat image for image discrimination, comparison, subtraction, and the like. As described in an article entitled "Spherical Transform of Fruit Images for On-line Defect Extraction of Mass Objects" in Optical Engineering Vol. 35, No. 2, pgs. 344–350, February, 1996, produced by the Society of Photo-Optical Instrumentation Engineers, and hereby incorporated by reference, Yang Tao describes spherical transform methods developed to solve the problem of detecting defects on spherical curved objects which are difficult to identify because of the object image boundary effect and successfully applies this transform to an automated defect sorter. The spherical transform is obtained by compensating the intensity gradiance on curved objects. Defects below the background level are extracted through a preservation transform. The defect extraction is enabled by a uniformly distributed plain image through 2-step transformations and the defect position is determined by allocation process. The results show the effectiveness of the processing methods for the high-speed on-line defect identification on fruit packing lines.

Figure 1C:
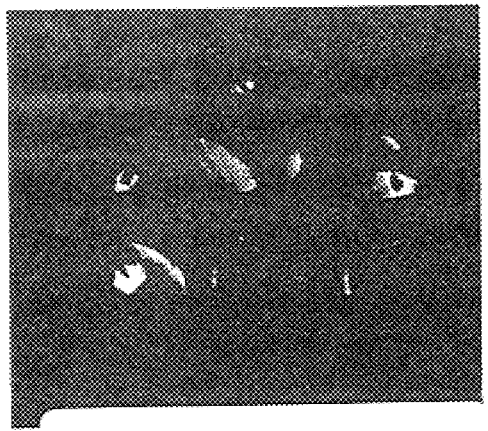
Figure 1B:
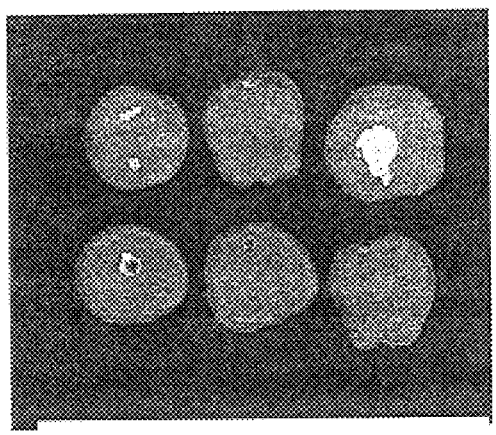
Figure 1D:
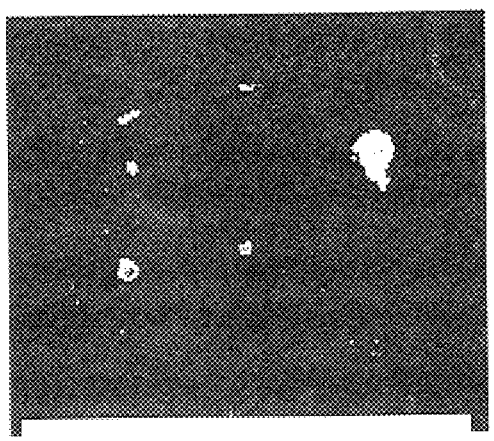

In accordance with the present invention, infrared camera color images (all gray level red/green) are converted to black and white images which are then compared and contrasted to one another to subtract out the nondefects such as stem-end, stem, and calyx to leave only true defects. As shown in FIGS. 1–4 of the drawings, simultaneous midinfrared (MIR) and near-infrared (NIR) images are taken of items or objects such as apples, processed, and then compared to determine if true defects exist. FIG. 1A is a photographic representation of an MIR color image of stem-ends, stems and calyx on apples lying on a conveyor in different orientations. The background image has been eliminated. FIG. 1C is a black and white processed image of FIG. 1A. FIG. 1B is a color NIR image depicting stems, stem-ends, calyx and defects. FIG. 1D is a black and white processed image of FIG. 1B. In accordance with the present invention, FIGS. 1C and 1D are processed, compared, contrasted, the stems, stem-end and calyx of FIG. 1C are subtracted from the image of FIG. 1D and there is left the true defects image which is processed and used to sort, grade, or separate the apples.

Figure 2A:
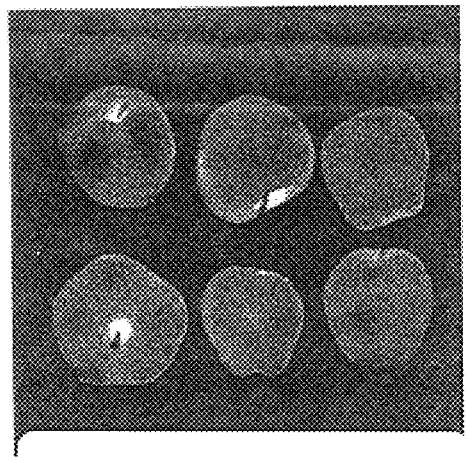
Figure 2C:
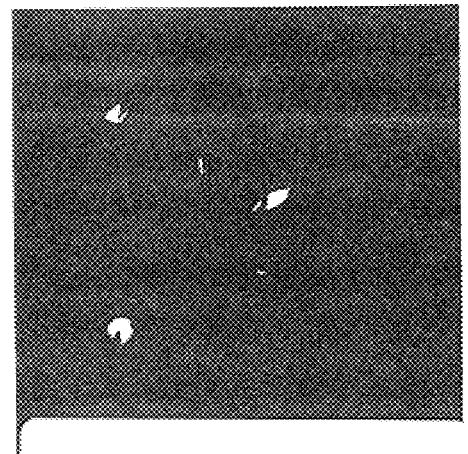
Figure 2B:
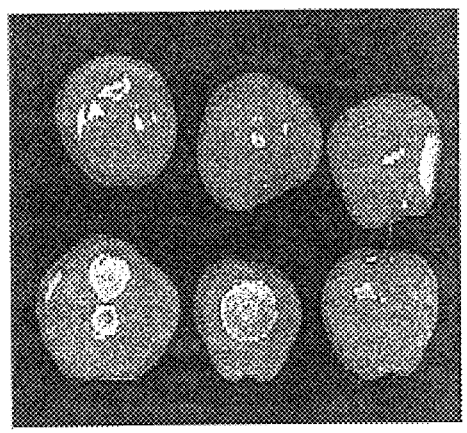
Figure 2D:
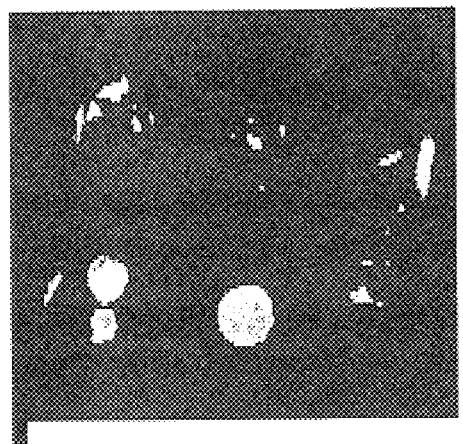
Figure 3A:
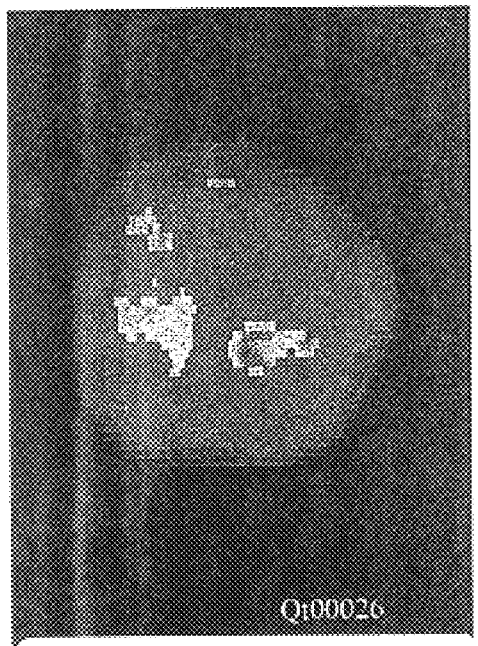
Figure 3C:
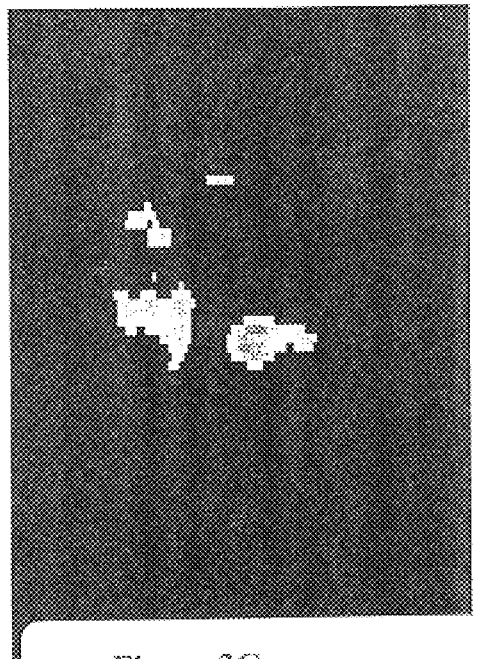
Figure 3B:
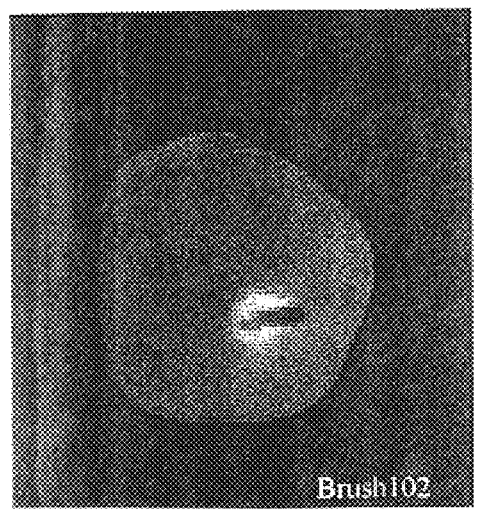
Figure 3D:
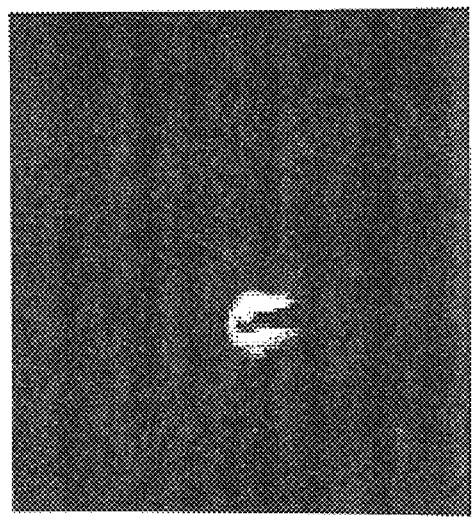
Figure 4A:
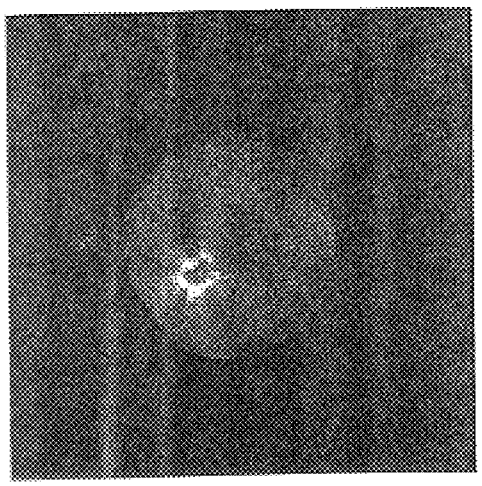
Figure 4C:
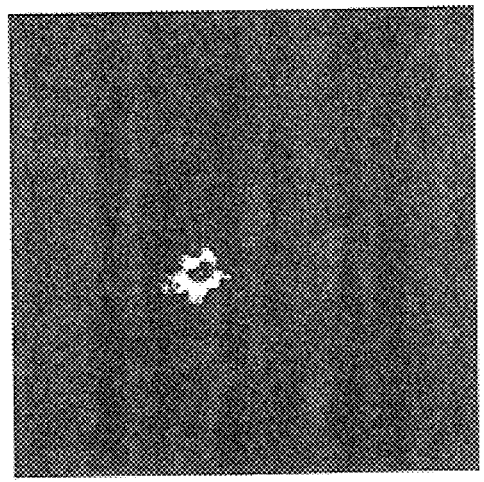
Figure 4B:
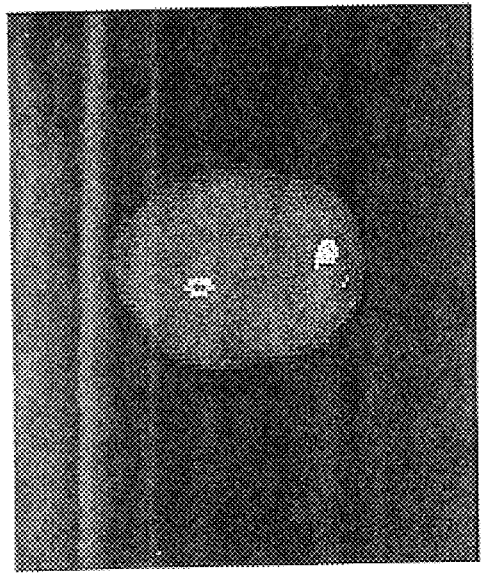
Figure 4D:
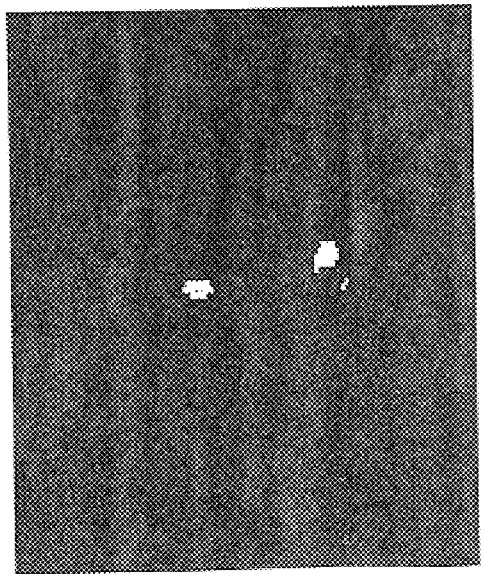
Figure 5:
Figure 6:
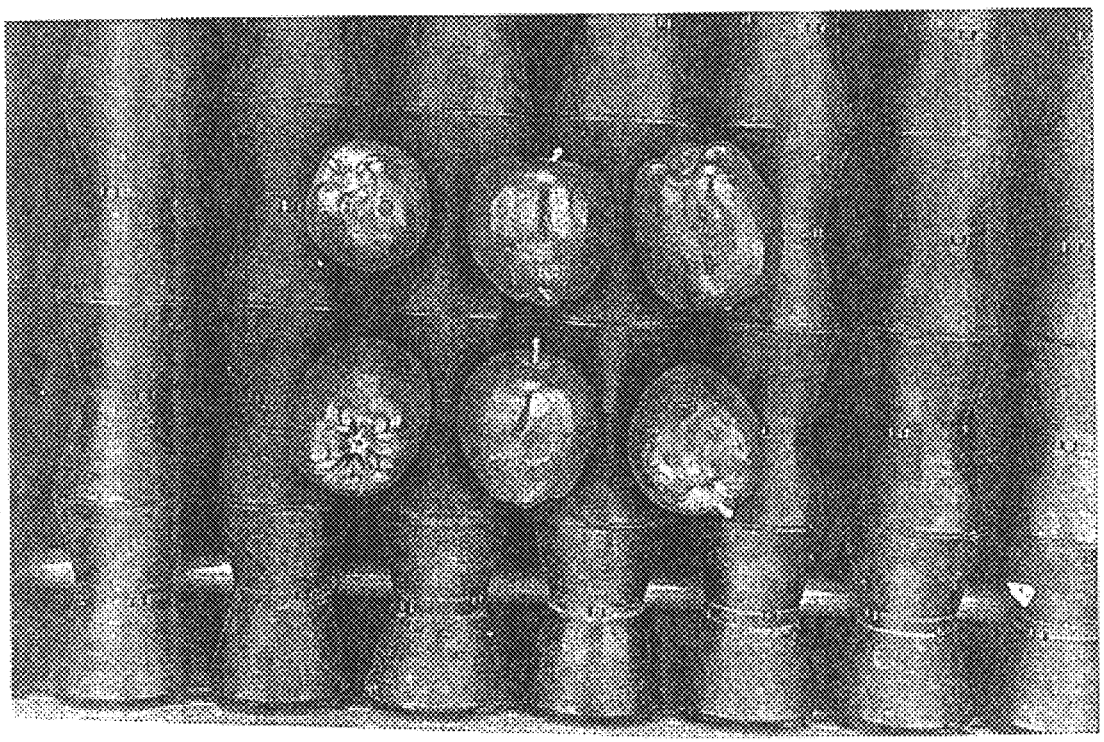
Figure 7:
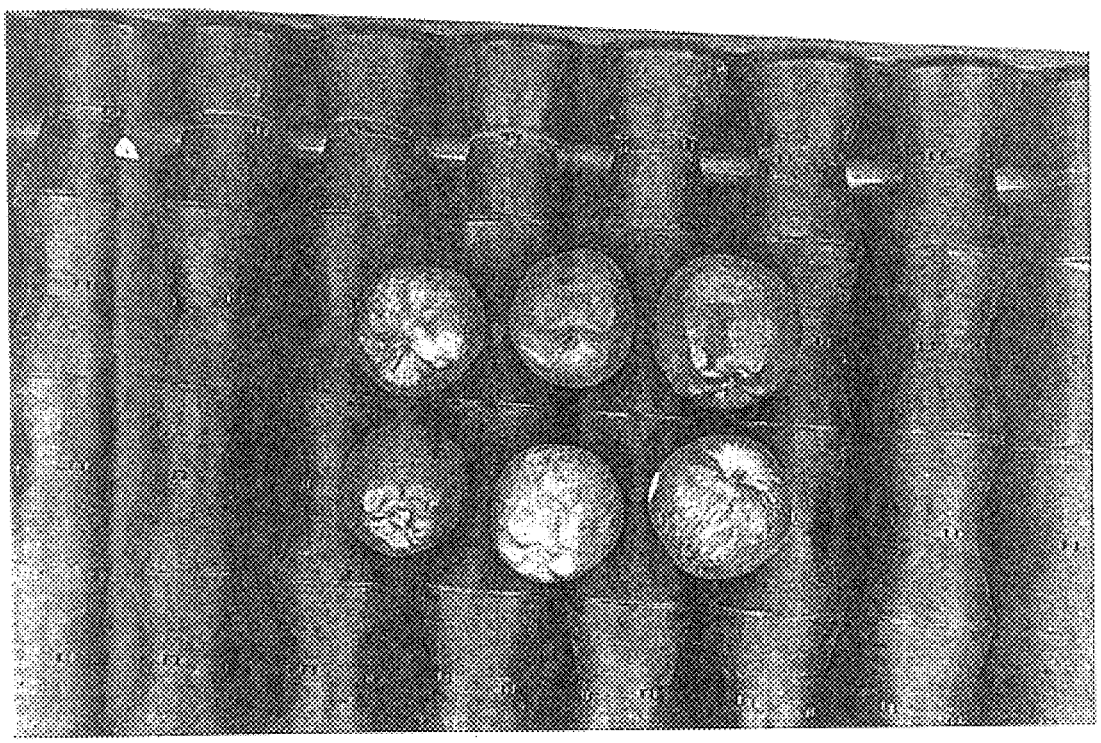
Figure 8:
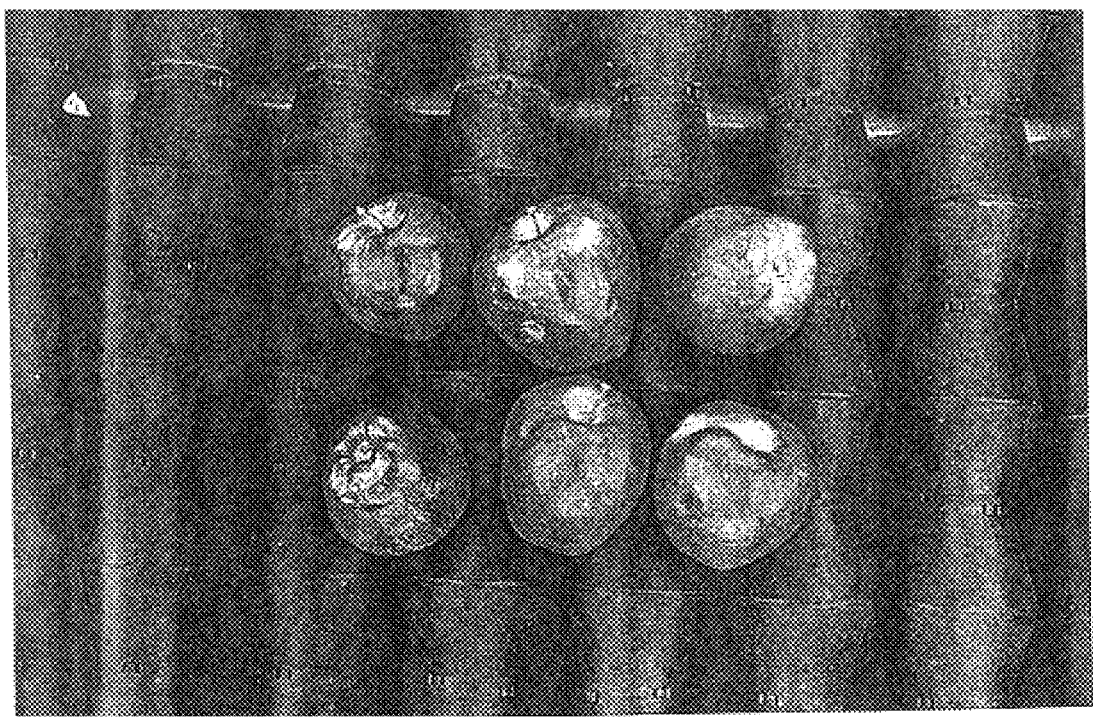

Similarly, FIG. 2A is a color MIR image and FIG. 2C is a black and white processed image from FIG. 2A. FIG. 2B is a color NIR image while FIG. 2D is a black and white processed image of FIG. 2B. Again, FIG. 2C is subtracted from FIG. 2D processed, and the like to determine true defects and which apples are sorted or separated.

FIGS. 3 and 4 highlight the stem end and calyx respectively of a single apple. FIG. 3A is a color NIR image and FIG. 3C is a black and white processed image of FIG. 3A. FIG. 3B is a color MIR image and FIG. 3D is a processed black and white image of FIG. 3B. FIG. 4A is an MIR image and FIG. 4C is a black and white processed image of FIG. 4A. FIG. 4B is a color NIR image and FIG. 4D is a black and white processed image of FIG. 4B.

FIGS. 5–8 are color photographic representations of different apple orientations on a roller conveyor as well as different true defects and provide a visual appreciation of the difficulty in comparing and contrasting true defects to stems, stem-end, and calyx of an apple or other fruit or vegetable.

Figure 9:
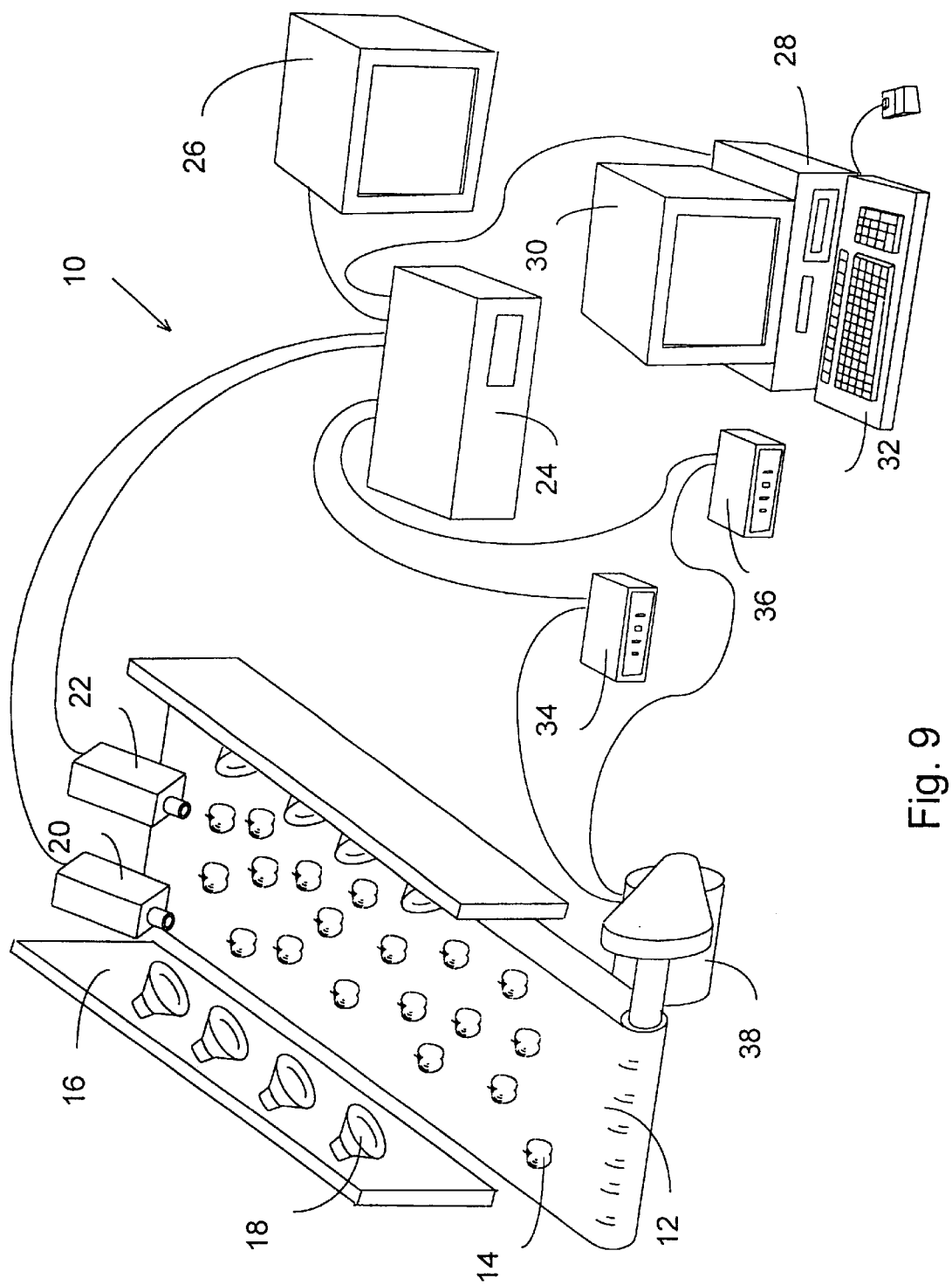
FIGS. 9–12, 13, 14, 17, 18, 20, 21, 26, 27, and 30 are schematic diagrams.

FIG. 9 is a schematic representation of a true defect identification and discrimination unit 10 in accordance with an exemplary embodiment of the present invention and including as system hardware a roller conveyor 12 supporting a plurality of apples 14, a light box 16 housing and plurality of lights 18, an NIR camera 20, an MIR camera 22, a digital image processing system or processor 24, an image monitor 26, a host CPU (486 computer) 28, a computer monitor or VGA 30, a computer keyboard 32, signal controls 34, driver controls 36, and a driver, separator, grader, sorter, bin drop control, or the like 38.

Figure 10:
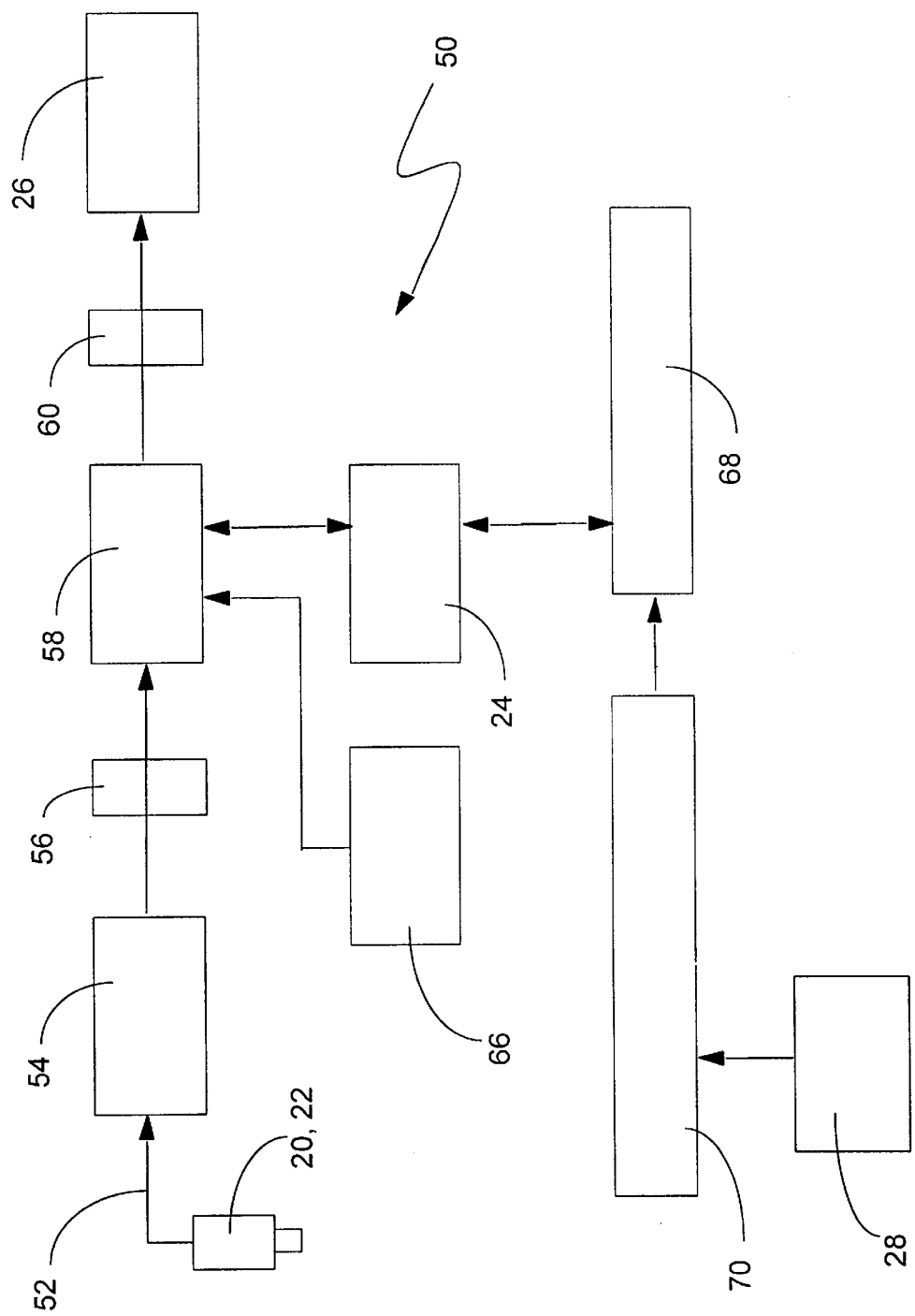

FIG. 10 is a schematic component and process flow diagram showing the processing of each camera image generally designated 50 and shown to include a camera which produces an analog image 52, an A/D analog to digital converter 54, an LUT 56, image ram 58, RAMDAL 60, and image monitor 26. The image ram receives and provides signals to a LUTS 66, processor 24, and processor 24. The processor 24 receives and provides signals to a FIFO 68 and a computer bus 70 which receives and provides signals to host computer 28.

Figure 11:
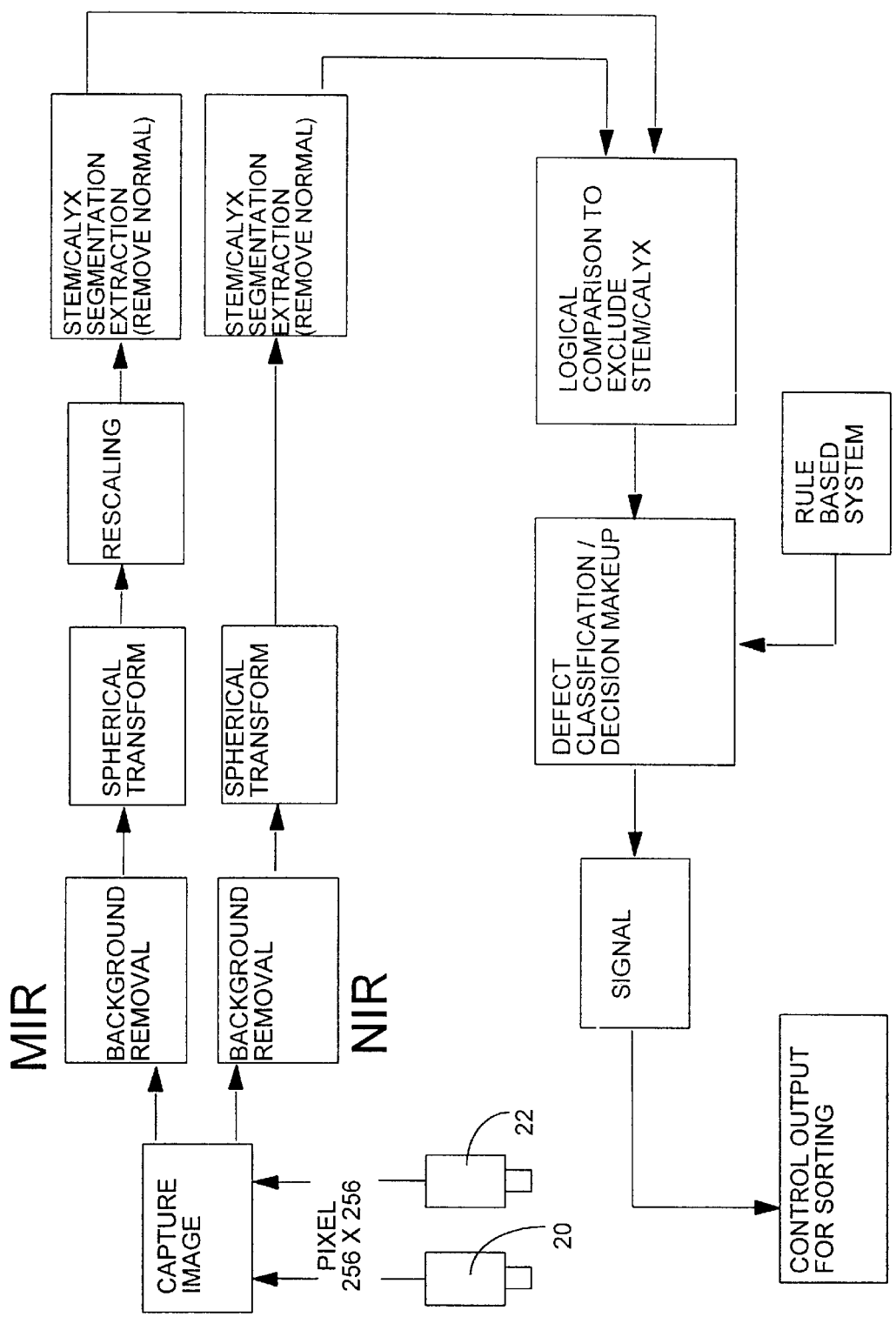

With reference to FIG. 11 there is shown a schematic diagram of the overall procedure or process wherein the images from the cameras 20 and 22 are captured and then the NIR image is processed to remove background, for a spherical transform, defect segment extraction, and the like prior to image comparison. The MIR image from camera 22 has the background removed, spherical transform, is rescaled to provide a common aspect ratio between the cameras and images, and then stem, calyx and defect segmentation and extraction and the like prior to logical comparison. The processed NIR and MIR images are logically compared to exclude stem-end, stem and calyx and then the remaining defects are classified, categorized, and quantified using a rule base system as well as user parameters to provide a control signal for sorting, grading, separating, and the like items or objects such as apples based on the amount, type, quantity, and character of the detected defects.

Figure 12:
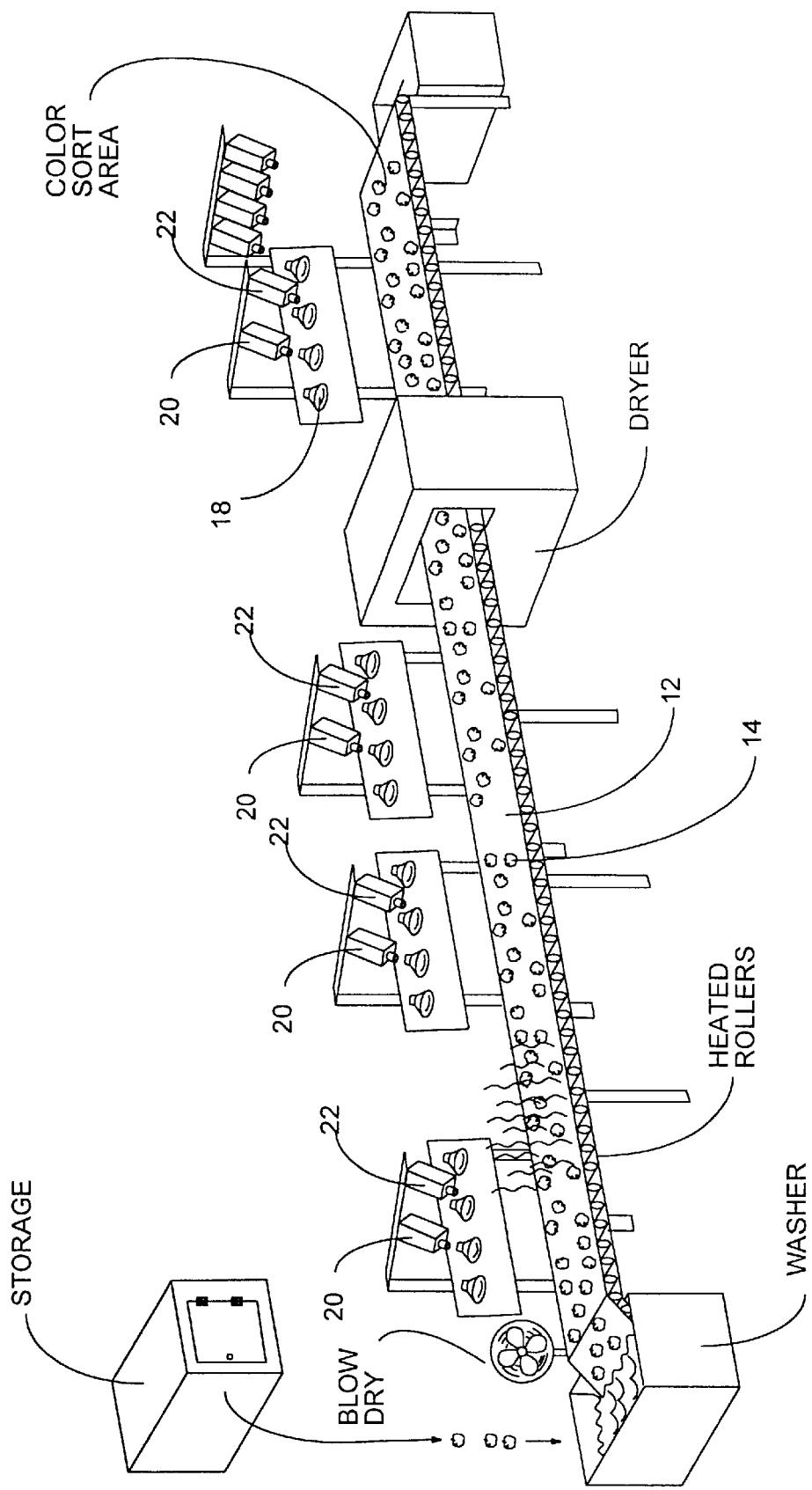

As shown in FIG. 12 a schematic overall operation or item packing system is shown wherein the NIR and MIR cameras and defect detection and discrimination system of the present invention is incorporated along the pack line either just downstream of the cleaning tank and blow dry, in the area of the dewax or clean, just upstream of wax application, or just downstream of the dryer. It is preferred to place the NIR/MIR defect inspection and sort system of the present invention as far upstream as possible so that rejected or sorted items are removed prior to additional processing and thereby reducing cost, increasing line capacity, and the like. Since the defect inspection and sorting system of the present invention relies on a change in temperature to provide a better discrimination of true defects from stem-end, stems, and calyx, it is preferred to use it just downstream of a heating sequence, a heating blow dry, in association with heated rollers or brushes, or downstream of the dryer.

In accordance with the present invention, the particular grader, sorter, separator, or the like, is not limited but it includes kickers, drop bins, pushers, gates, robotic arms, and/or the like.

Dual-camera NIR/MIR Imaging for Stem-end/Calyx Identification in Apple Detect Sorting One of the persistent problems involved in the technology of automated machine vision apple defect sorting lies in the discrimination between true defects and the stem-end/calyx of fruit. To solve this problem, a novel method was developed which incorporates a near-infrared (NIR) camera and a mid-infrared (MIR) camera for simultaneous imaging of the fruit being inspected. The NIR camera is sensitive to both the stem-end/calyx and true defects; while the MIR camera is only sensitive to the stem-end and calyx. True defects can be quickly and reliably extracted by logical comparison between the processed NIR and MIR images. A 98.86% recognition rate for stem-ends and a 99.34% recognition rate for calyxes were achieved using a dual-camera NIR/MIR machine vision defect sorting system.

Keywords: machine vision; infrared; imaging; defect; stem-end; calyx; inspection; fruit.

Introduction

Fruit such as apples are sorted and graded according to color, shape, and size of the fruit, as well as the amount of defects on each apple. The currently available commercial apple sorting equipment is generally limited to systems for measuring the color, shape, and size of fruit (Tao, 1998). So far there is no method or system that is effective for automated recognition and sorting of apple defects. Although considerable effort has been made in the field of automated machine vision inspection of fruit defects (Graf, 1982; Throop and Aneshansley, 1993; Tao, 1996), one of the difficult problems remains for a long time. This persistent problem is how to distinguish the stem-end (stem cavity) and calyx (bloom bottom) from true defects such as bruises, rots, and limb rubs. During a machine vision inspection process, once the stem-end or calyx appears in the field of view of the imaging camera, they could be mistakenly identified as defects, because they are similar to true defective spots in the image. Therefore, there is a need for an effective method and system for on-line recognition and separation of apple defects and stem-end/calyx.

To solve the persistent problem of being unable to distinguish the true defects from stem-ends/calyxes in fruit images, three approaches were proposed. The first one is to develop a mechanical device such as a system rollers and half-wheels which would be able to orient the apples to avoid the stem-ends and calyxes being observed by the camera. If fruit could be oriented by a mechanical system so that their axis of rotation passes through the stem-end and calyx, it would be an ideal mean to the system design and it would make image processing tasks much easier. However, the difference between apple height and width, fruit shape, size, stem-end stiffness and length, and surface curvature appear to play a role in apple orientation. To date, there is no device on the market that will automatically orient 100% of apples. A mechanical apparatus developed by Sarker and Wolfe (1985) was used for aligning tomatoes along the stem-calyx axis, but it can not be used for orient apples. Tennes et al. (1969, 1970) investigated several mechanical principles for separating cherries without stems from those with attached stems. Their methods would not be suitable for other fruit which are more susceptible to bruising or have shorter stems. Troop et al. (1997) tested a commercial bicone roller conveyor for move orient apples. Only approximately 60% of the fruit could be successfully oriented for some apple cultivars.

The second approach uses image processing techniques to detect fruit stem-end and calyx whenever they appear in the camera's field of view. Wolf and Sandler (1984) developed a stem detection algorithm based on a syntactic analysis of fruit contours in images. Miller and Delwiche (1989) used the variance of image gradient directions within a segmented area to identify concave surfaces around fruit stems. The reported classification error for identifying the stem-end of a peach as a defect was about 30%. The high rejection rate and the time-consuming calculation would not make this method feasible for commercial application.

The third approach is based on 3D reconstruction techniques, especially the structured light range imaging; to detect the surface geometry of the fruit. Yang (1993) used structured lighting to detect stem-end and calyx. His method combined the results from the damage detection algorithm with the information obtained from the changes in slope of the structured light projections. Crowe and Delwiche (1996a, b) also tried to detect stem-end and calyx using structured illumination. U.S. Pat. No. 5,526,119 to Blit et al. (1996) discloses a fruit inspection method including a stem/calyx identifier to find the locations of the stem and calyx. Locations are identified as putative stem or calyx locations if the curvature of the grid lighting lines, superimposed on those locations, changes relatively sharply thereat. Use of the structured lighting technique has some obstacles for implementation in automated inspection. The major problem with structured lighting is the misclassification of the laser lines on the image. This leads to an erroneous interpretation of the scene. Due to the randomness of the running fruit, it is very difficult to detect the deformations of the lighting patterns on the fruit surface and get anomalous image patterns analyzed, especially when scanning multiple apples in the viewing area.

The object of this research was to develop a new near-infrared (NIR) and mid-infrared (MIR) synergetic machine vision method and system for automatic fruit defect inspection. More particularly, the present research aims at solving the persistent difficulty in distinguishing stem-ends/calyxes from true defects in apples.

Method and System

1. Method

The difference in light reflectance of object surfaces provides useful information for using machine vision to distinguish the defective and good apples. Test showed that the reflectance in the NIR range between 700 nm and 2000 nm is less for bruised areas than unbruised areas on apples (Brown et al., 1974). Usually CCD cameras with optical filters as attachments are employed in machine vision defect inspection systems. The effective wavelengths of such vision systems are generally limited to an NIR range between 700 nm and 1000 nm. However, the NIR range from 700 nm to 1000 nm is sensitive not only to defects but also to the stem-end and calyx on fruit. Separation of true defects from the stem-end and calyx using only NIR camera (i.e. CCD camera attached with a selected optical filter) is very difficult.

To solve this problem, two imaging devices (an NIR camera and an MIR camera) are incorporated. The NIR camera at 700 nm to 1000 nm wavelength range is used to provide an image of stem-ends, calyxes, and defects in apples. The MIR camera at 3 μm to 5 μm or 8 μm to 12 μm is insensitive to true defects and is used to provide an image of only stem-ends and calyxes. The 5 μm to 8 μm spectral range is avoided because it is sensitive to hot air. Thus, an image of only true defects can be obtained by subtracting the MIR image from the NIR image. The image of only true defects are then analyzed to generate the separation or sorting signals using a rule-based system as well as user parameters.

Figure 13:
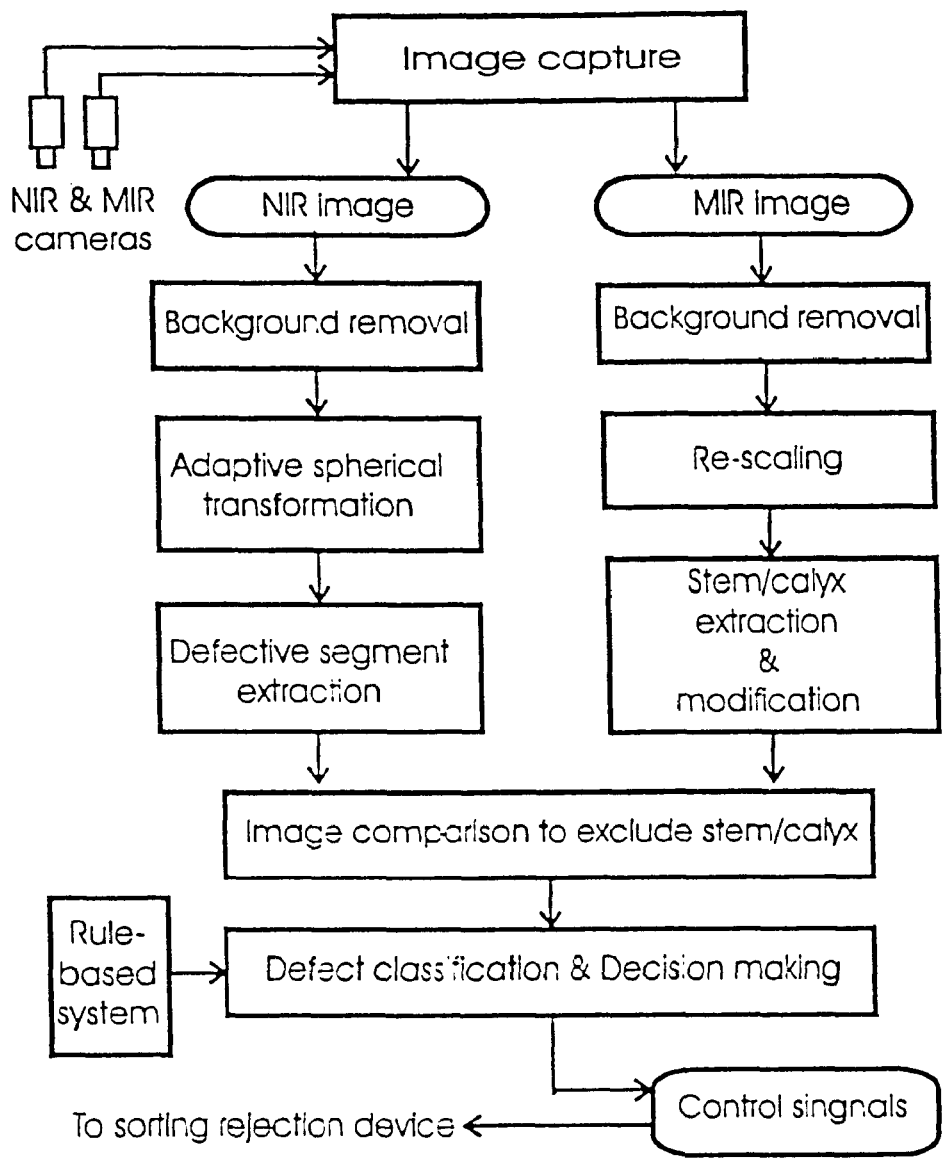

FIG. 13 is a schematic diagram of the overall inspection procedure wherein the NIR and MIR images from the cameras are first captured. Both the NIR and the MIR images are processed prior to image comparison. First, the background of the NIR image is removed. Then an adaptive spherical optical transform (Wen and Tao, 1997) is applied to convert the curved NIR object image (due to the boundary light reflectance effect of substantially spherical objects) into a flat image. The adaptive spherical transform also provides sufficient flexibility to cope with the natural variations in brightness and size among the fruit. Finally, an image which contains both stem-ends/calyxes and various defect segments is obtained after the defective segment extraction stage using a global thresholding. On the other hand, the MIR image has the background removed, is re-scaled to provide a common aspect ratio between the cameras and images. Then an image of stem-ends/calyxes is obtained through stem/calyx extraction operation. The modification to the obtained stem-end/calyx image is made to fill the holes and eliminate the noises in the stem-end/calyx areas. The processed NIR and MIR images are compared to exclude stem-ends and calyxes. The remaining defects are classified and quantified using a rule-based system as well as user parameters to provide control signals for sorting, grading, and separating the objects, such as apples, based on the amount, type, quantity, and character of the defects.

2. System

Figure 14:
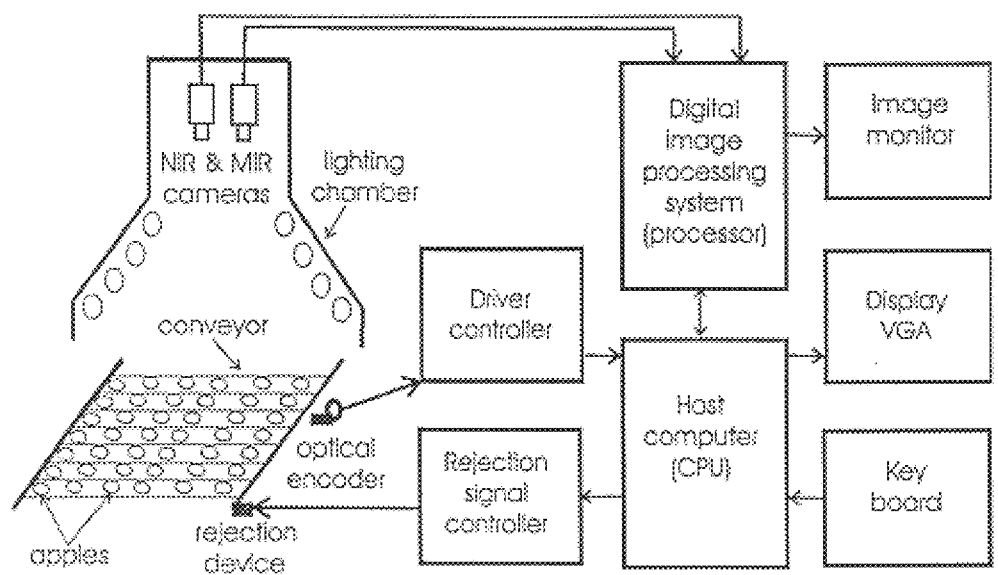

FIG. 14 is a schematic representation of the whole system. It consists of both NIR and an MIR cameras for fruit imaging, a lighting chamber for providing uniform illumination on the field of view, a roller conveyor for supporting and moving apples, a digital image processor, an optical encoder for providing the timing signal for on-line mechanical and electronic synchronization, and a host computer. The apparatus has a capability of inspecting 3000 apples per minute.

Test Results

Test samples of both good and defective 'Red Delicious' apples were obtained from a commercial apples packing plant. A total of 400 apples (220 good apples and 180 defective apples) were selected for testing. The defects on samples included bruises, limb rubs, bull's eyes, rots, cuts, worm holes, scars, and black spots. Samples were refrigerated at about 4° C. until the test. The orientations of the test samples on conveyor were randomly selected by hand. A total of 176 stem-ends and 152 calyxes appeared in the filed of view of camera and required to be distinguished from true defects during the test.

Figure 15:
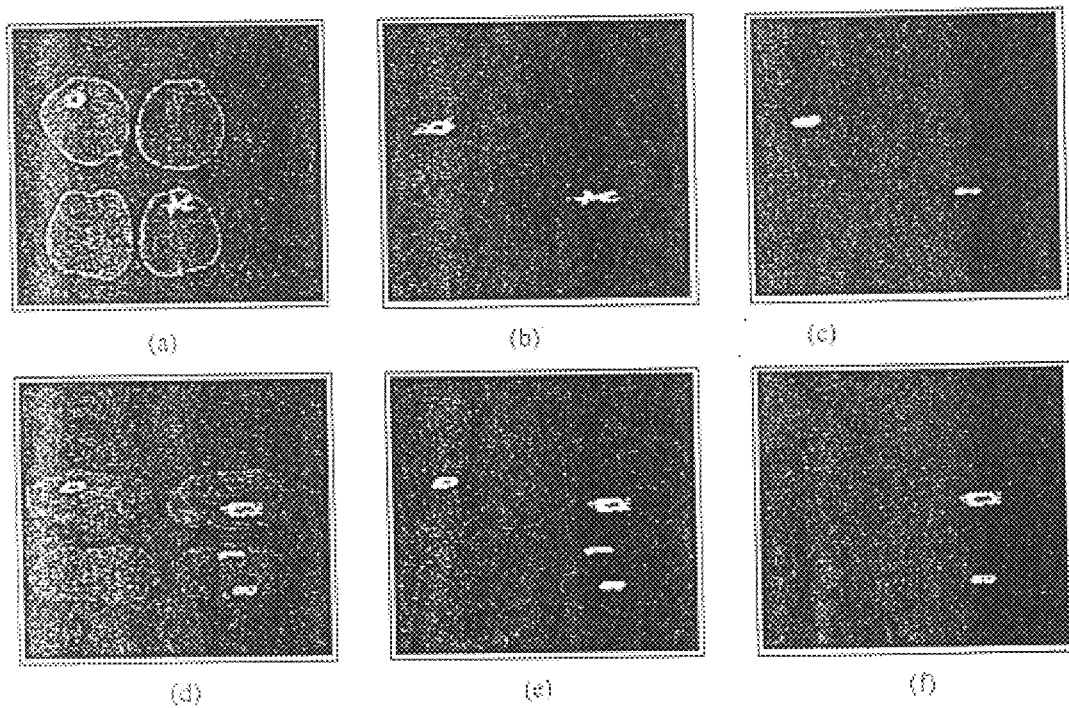

FIG. 15 photographically shows how true defects can be obtained from NIR and MIR images taken simultaneously of apples. FIG. 15(a) is an MIR image, with background removed, of four apples lying on a conveyor. The apples are so oriented that the stem-end of the top-left apple and the calyx of the bottom-right apple appear in the camera's field of view. Remember that the two apples in the left column are good, the top-right apple is bruised, and the bottom-right apple has a scar defect on it. FIG. 15(b) is the extracted stem-end/calyx image from a re-scaled image of FIG. 15(a). FIG. 15(c) is the modified stem-end/calyx image of FIG. 15(b), where the holes and the noise in stem-end/calyx areas have been removed. FIG. 15(d) is an NIR image of the same apples, in which the stem-end, calyx, and defects are depicted by yellow pixels. FIG. 15(e) is a processed image through defect segment extraction, in which both defects and stem-end/calyx are detected. FIG. 15(c) and 3(e) are compared, resulting in FIG. 15(f) in which the stem-end and calyx are excluded and only true defects are obtained for further processing, sorting, and grading of apples.

Figure 16:
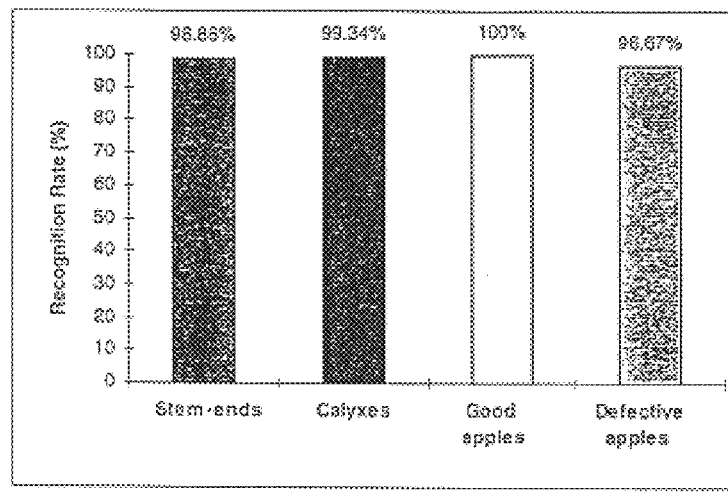
FIGS. 16, 19, 22, 29, 31, and 32 are graphical representations or illustrations.
Figure 17:
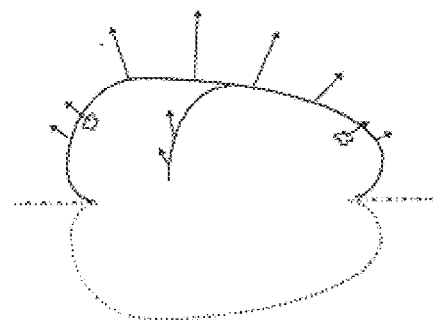
Figure 18:
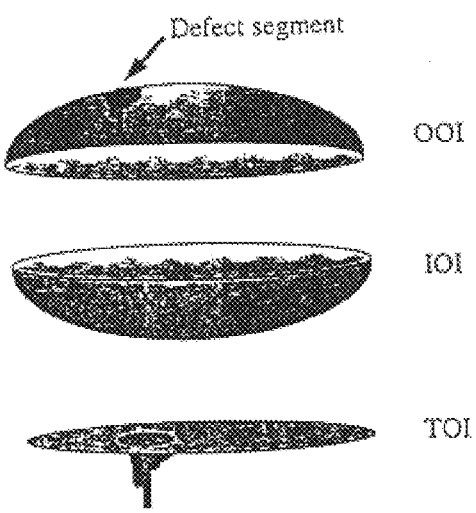
Figure 19:
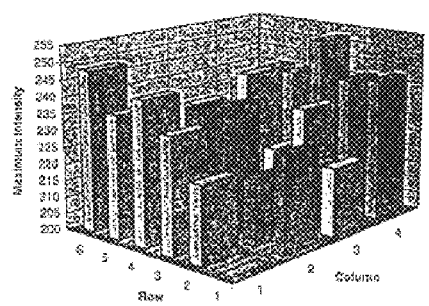
Figure 21:
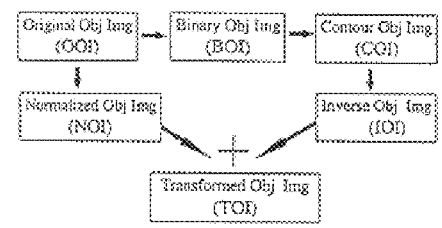
Figure 20:
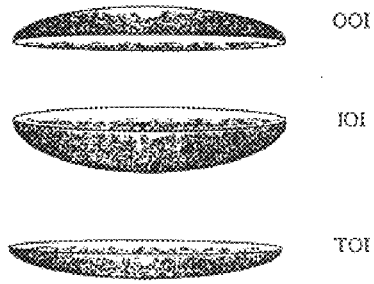
Figure 22:
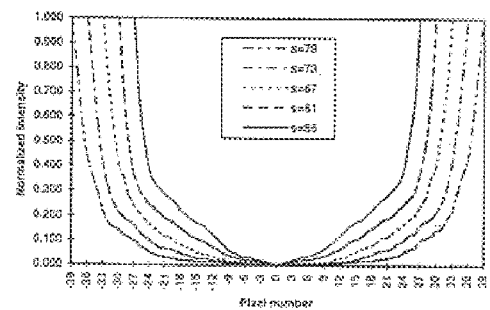
Figure 23:
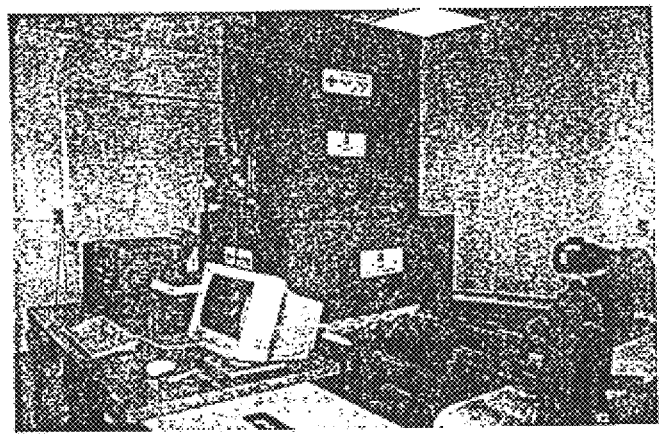
Figure 26:
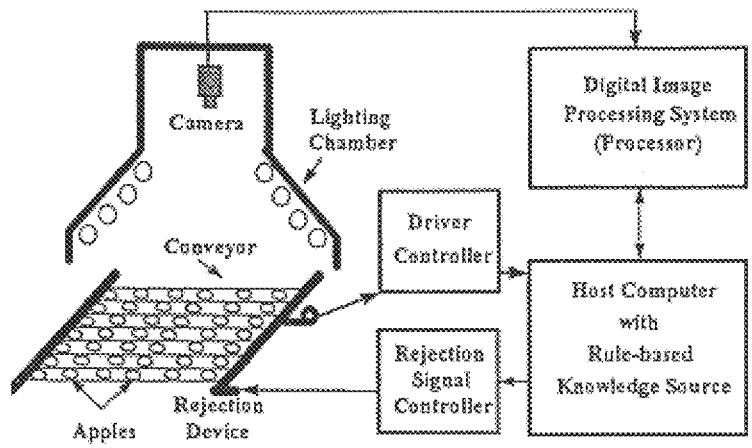
Figure 27:
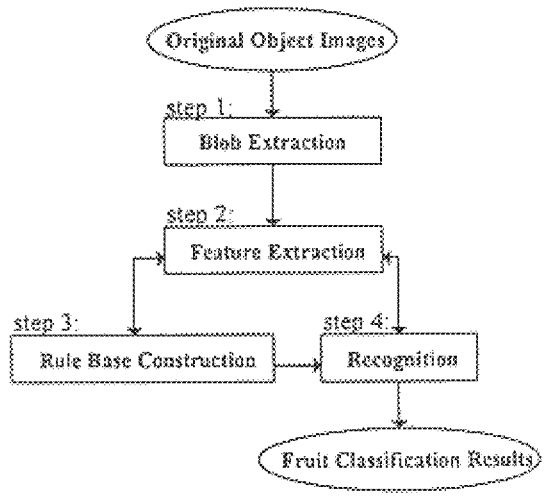
Figure 24:
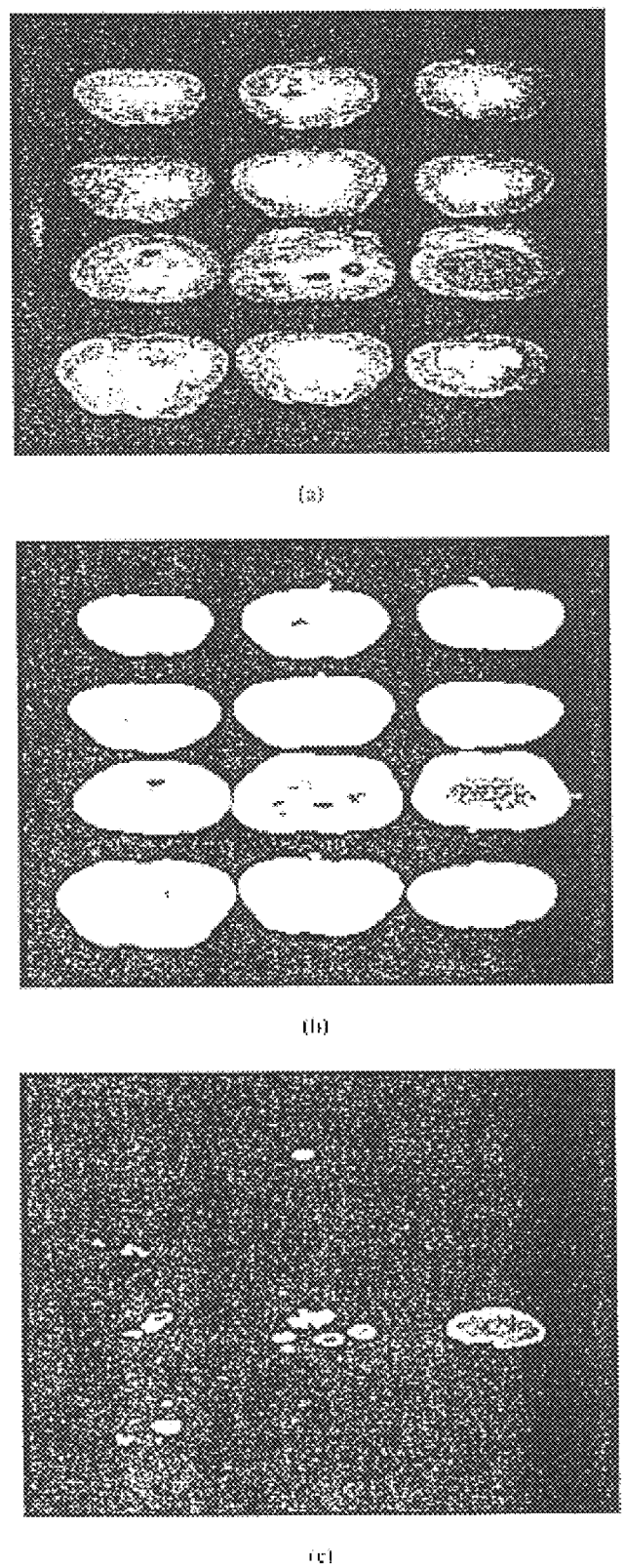
Figure 25:
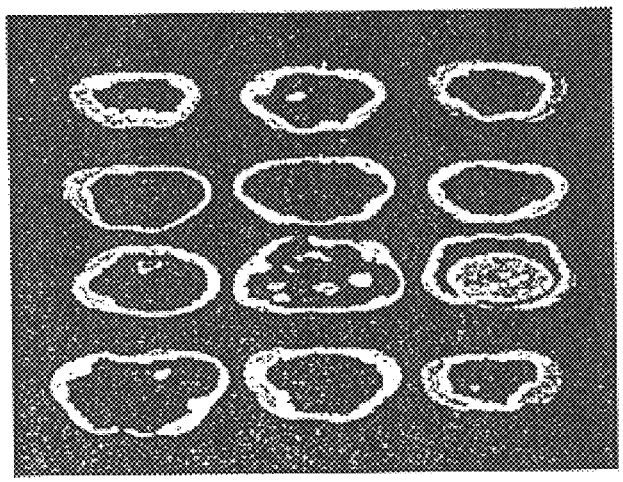
Figure 25:
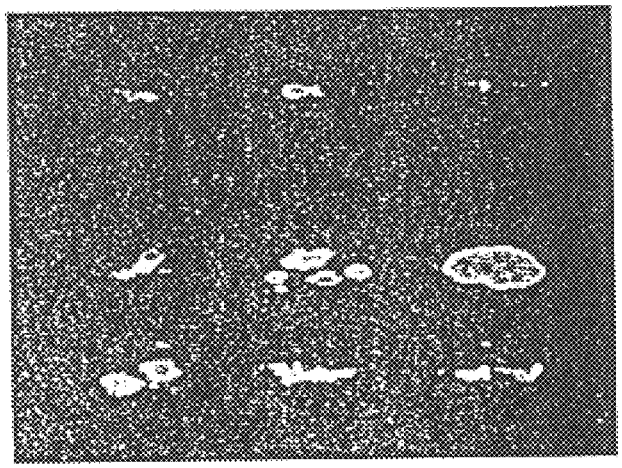
Figure 25:
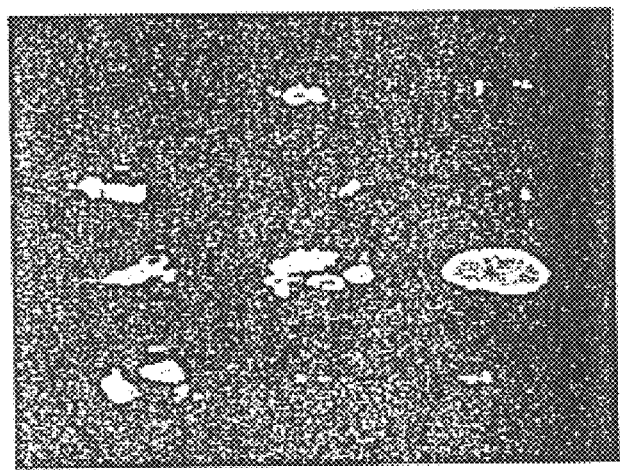
Figure 28:
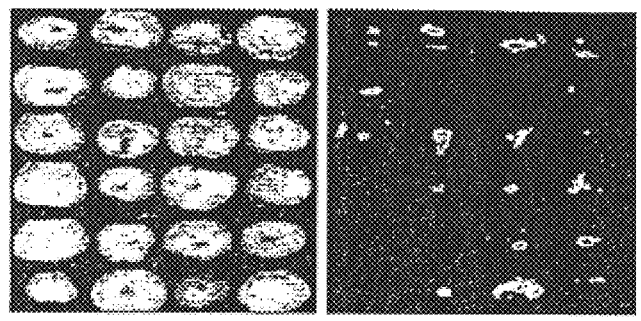
Figure 29:
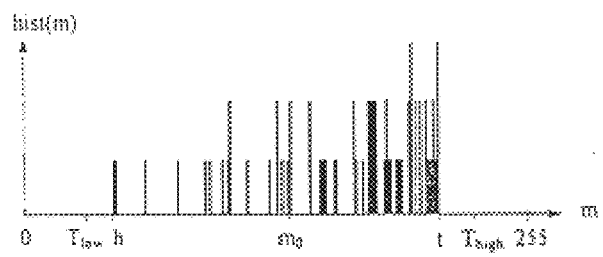
Figure 31:
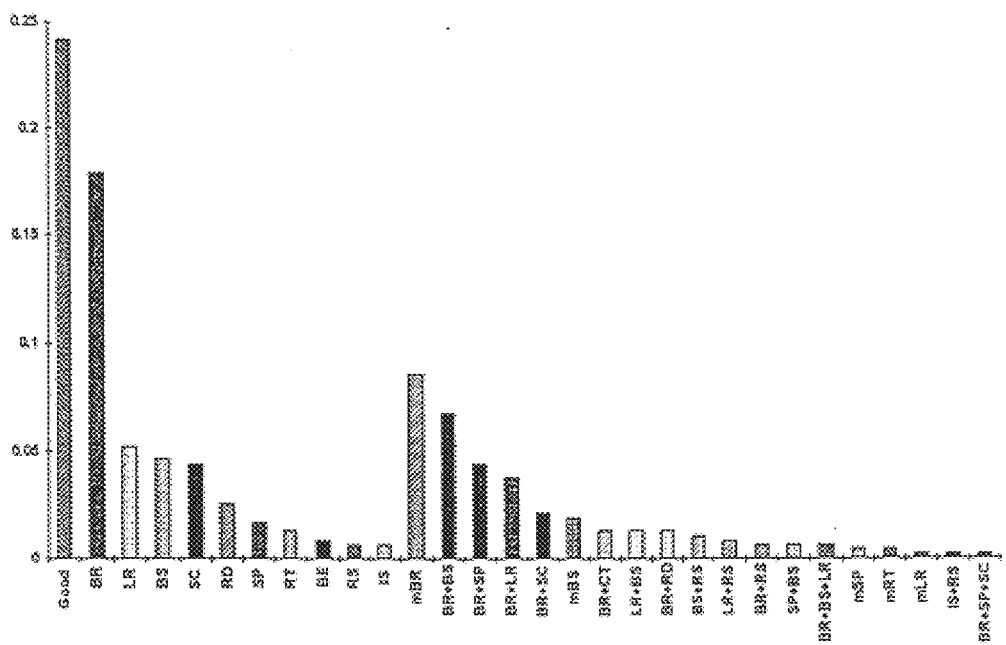
Figure 30:
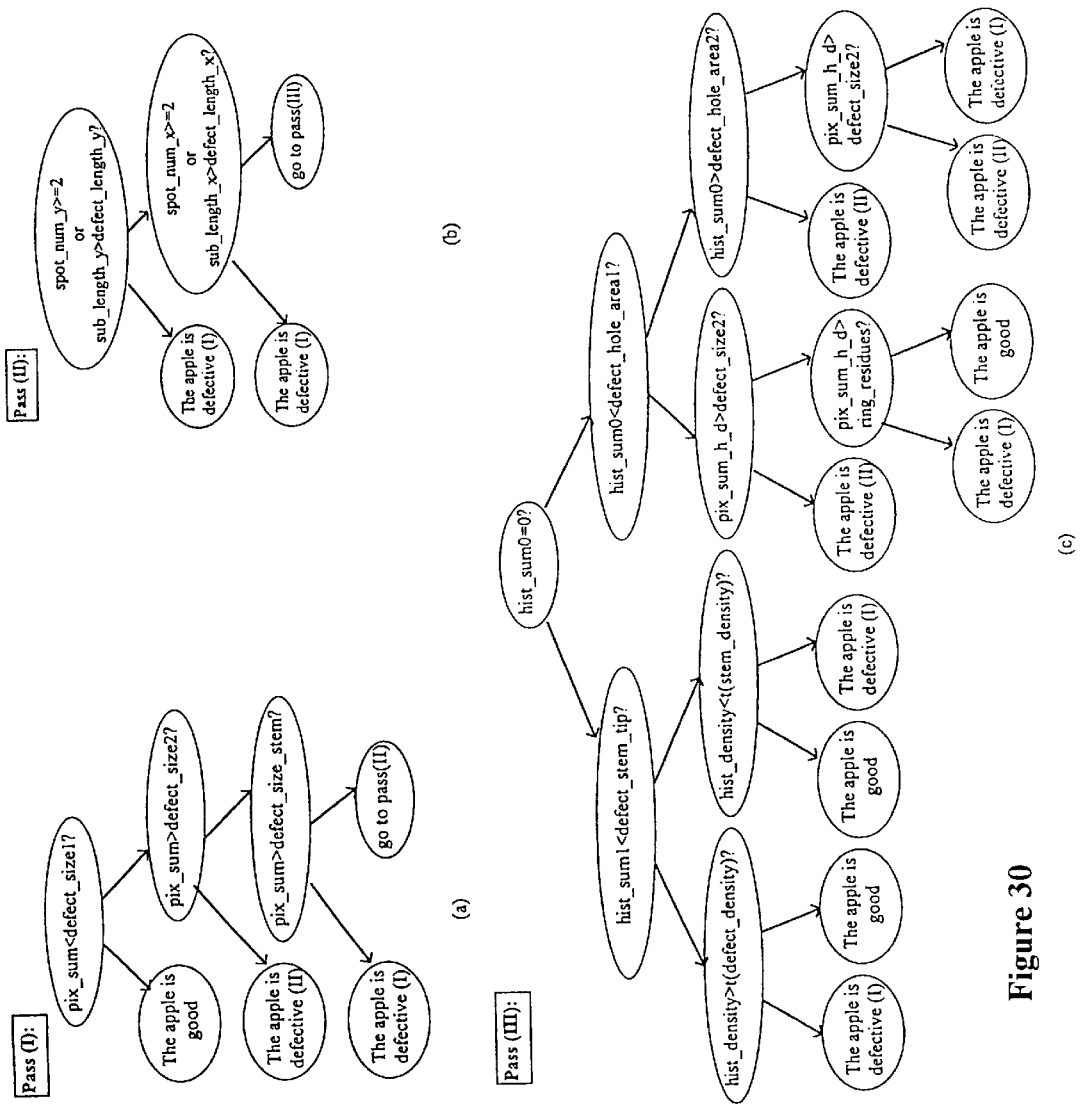
Figure 32:
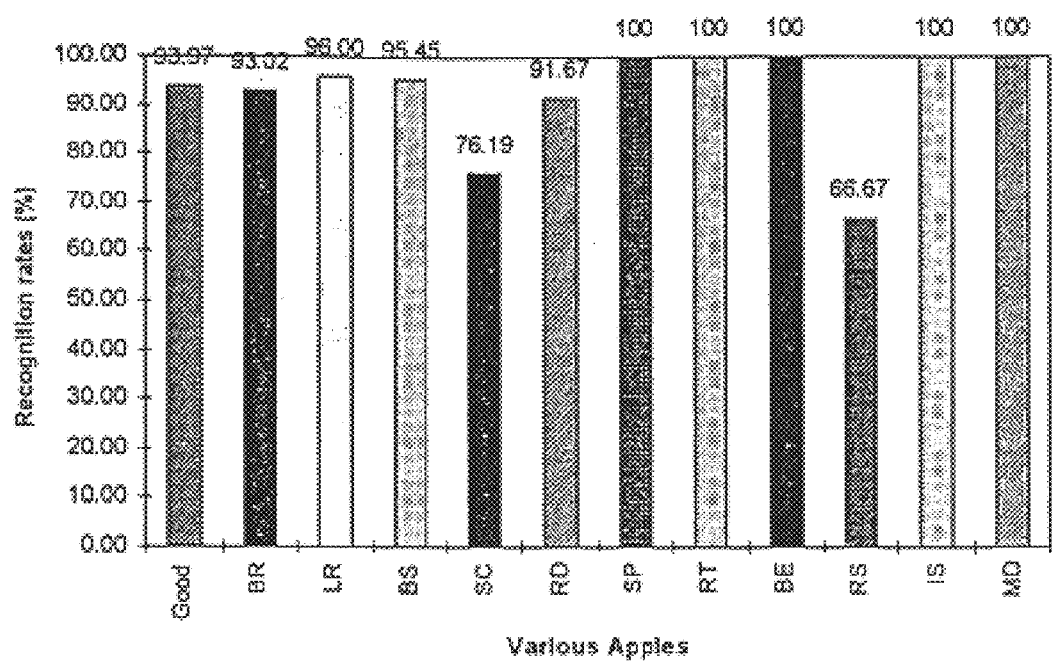

The total recognition rates for stem-ends and calyxes were shown in FIG. 16. Near 100% recognition rates (98.86% for stem-ends and 99.34% for calyxes) were achieved, which were much higher than those obtained by other methods using mechanical devices, imagine processing, and/or laser structured lighting. When the stem-end (or calyx) appeared at the edge of an apple image, mis-recognition could sometimes happened. FIG. 16 also gave the recognition rates for good and defective samples. All good apples were correctly recognized as good. The recognition rate for defective apples was 96.67%.

CONCLUSIONS

A dual-camera NIR/MIR imaging method was successfully developed for apple defect recognition and stem-end/calyx identification. The NIR camera at the 700 nm to 100 nm range is sensitive to both stem-ends/calyxes and true defects; while the MIR camera at the 3 μm to 5 μm (or 8 μm to 12 μm ) range is only sensitive to stem-ends and calyxes. An NIR image containing stem-ends/calyxes and defective segments is obtained using an adaptive spherical transform technique. Meanwhile, an MIR image of the stem-ends and calyxes is generated from the original MIR image. Then, true defects can be quickly and reliably extracted by logical comparison of the processed NIR and MIR images. Therefore, the method presented herein effectively solves the problem that scientists and engineers have been having for many years of being unable to separate stem-ends/calyxes from true defects in apple defect sorting. This technique can also be applied to inspection of other fruits with stem-end and calyx, such as peaches, pears, and tomatoes.

Acknowledgements

The authors gratefully acknowledge the funding support from the U.S. Department of Agricultural (USDA) SBIR program and Agri-Tech, Inc.

REFERENCES

Blit, S., E. Bartfeld, I. Pais, Y. Eilam; E. Vallach, H. Bezdin, I. Laron, D. Katzin, A. Reichart, and J. Samekh. 1996. Apparatus & method for inspecting articles such as agricultural produce. U.S. Pat. No. 5,526,119.

Brown, G. K., L. J. Segerlind, and R. Summit. 1974. Near-infrared reflactance of bruised apples. Trans. of the ASAE 17(1):17–19.

Crowe, T. G. and M. J. Delwiche. 1996a. Real-time defect detection in fruit-Part I: Design concepts and development of prototype hardware. Trans. of the ASAE 39(6):2299–2308.

Crowe, T. G. and M. J. Delwiche. 1996b. Real-time defect detection in fruit-Part II: An algorithm and performance of a prototype system. Trans. of the ASAE 39(6):2309–2317.

Graf, G. L. 1982. Automatic detection of surface blemishes on apples using digital image processing. Ph.D. thesis. Cornell University, Ithaca, N.Y.

Miller, B. K. and M. J. Delwiche. 1989. A color vision system for peach grading. Trans. of the ASAE 32(4):1484–1490.

Miller, B. K. and M. J. Delwiche. 1991a. Spectral analysis of peach surface defects. Trans. of the ASAE 34(6):2509–2515.

Miller, B. K. and M. J. Delwiche. 1991b. Peach defect detection with machine vision. Trans. of the ASAE 34(6):2588–2597.

Pen, C. L., W. K. Bilanski, and D. R. Fuzzen. 1985. Classification analysis of good and bruised peeled apple tissue using optical reflectance. Trans. of the ASAE 18(1):326–330.

Rehkugler, G. E. and J. A. Throop. 1986. Apple sorting with machine vision. Trans. of the ASAE 29(5):1388–1397.

Rehkugler, G. E. and J. A.Throop. 1989. Image processing algorithm for apple defect detection. Trans. of the ASAE 32(1):267–272.

Sarker, N. and R. R. Wolfe. 1985. Computer vision based system for quality separation of fresh market tomatoes. Trans. of the ASAE 28:1714–1718.

Stiefvater T. L. 1970. Investigation of an optical apple bruise detection technique. M.S. These, Cornell University, Ithaca, N.Y.

Tao, Y. 1996. Spherical transform of fruit images for on-line defect extraction of mass objects. Opt. Eng. 35(2):344–350.

Tao, Y. 1998. Defective object inspection and separation system using image analysis and curvature transformation. U.S. Pat. No. 5,732,147.

Tennes, B. R., J. H. Levin, and C. M. Hansen. 1970. A machine for separating cherries without stems from those with attached stems. Trans. of the ASAE 13(5):539–546.

Tennes, B. R., J. H. Levin, and B. A. Stout. 1969. Sweet cherry properties useful for designing harvesting and handling equipment. Trans. of the ASAE 12(5):710–714.

Throop, J. A. and D. J. Aneshansley. 1993. Investigation of texture analysis features to apple bruises. ASAE Paper No. 933527. St. Joseph, Mich.:ASAE.

Throop, J. A., D. J. Aneshansley, and B. L. Upchurch. 1997. Apple orientation on automatic sorting equipment. Proc. Sensors for Nondestructive Testing:328–342. Orlando, Fla.

Upchurch, B. L., H. A. Affeldt, W. R. Hruschka, K. H. Norris, and J. A. Throop. 1990. Spectrophotometric study of bruises on whole, 'Red Delicious' apples. Trans. of the ASAE 33(2):585–589.

Wolf, R. R. and W. E, Sandler. 1984. An algorithm for stem detection using digital image processing. Trans. of the ASAE 28:641–644.

Wen, Z. and Y. Tao. Adaptive spherical transform of fruit images for high-speed defect detection. ASAE Paper No. 973076. St. Joseph, Mich.:ASAE.

Yang, Q. 1993. Finding stalk and calyx of apples using structured lighting. Comput. Electron. Agric. 8:31–42.

Yang, Q. 1994. An approach to apple surface feature detection by machine vision. Comput. Electron. Agric. 11:249–264.

What is claimed is:

1. A method for detecting defects in objects or items, comprising the steps of:

capturing images of the passing objects using two separate imaging devices, one near-infrared and one mid-infrared;

removing the background information from the images of the objects;

subjecting the object images to a spherical optical transform and a defect preservation transform to preserve any defect levels on objects and compensate for the non-lambertian gradient reflectants on spherical objects at their curvatures and dimensions;

subtracting the processed images provided by said mid-infrared device from the processed images provided by said near-infrared device to produce an image of just defects; and, analyzing the defect image to produce separation or sorting control signals based upon defect rejection decisions and user parameters to separate objects with defects from those that do not contain defects or to sort or categorize objects based on the amount, type, size or character of the defects.

2. The method as recited in claim 1, further comprising the step of raising the exterior surface temperature of each item or object to be inspected by about 5 to 15 degrees C. or more so that the infrared devices can provide an image of a difference in temperature between outer smooth health surface and the cavity at the stem-end, the stem, and calyx or similar depression, cavity, or protrusion.

3. The method as recited in claim 1, wherein at least a portion of the exterior surface of each item or object to be inspected is contacted by heated brush rollers to quickly heat the exterior of the objects passing along a conveyor to provide the necessary change in temperature to allow the infrared devices to provide an image of defects, stem-end, stem, calyx, depression, cavity, or protrusion.

* * * * *